United States Patent
Jervis et al.

(10) Patent No.: US 12,005,436 B2
(45) Date of Patent: Jun. 11, 2024

(54) DEVICES AND METHODS FOR SEPARATING PARTICLES FROM A LIQUID

(71) Applicant: Stemcell Technologies Inc., Vancouver (CA)

(72) Inventors: Eric Jervis, Vancouver (CA); Tom Glawdel, Toronto (CA)

(73) Assignee: StemCell Technologies Inc., Vancouver (CA)

(*) Notice: Subject to any disclaimer, the term of this patent is extended or adjusted under 35 U.S.C. 154(b) by 265 days.

(21) Appl. No.: 16/615,877

(22) PCT Filed: May 25, 2018

(86) PCT No.: PCT/CA2018/050615
§ 371 (c)(1),
(2) Date: Nov. 22, 2019

(87) PCT Pub. No.: WO2018/213935
PCT Pub. Date: Nov. 29, 2018

(65) Prior Publication Data
US 2020/0114345 A1 Apr. 16, 2020

Related U.S. Application Data

(60) Provisional application No. 62/511,503, filed on May 26, 2017.

(51) Int. Cl.
*B01L 3/00* (2006.01)
(52) U.S. Cl.
CPC ............. *B01L 3/502* (2013.01); *B01L 3/5082* (2013.01); *B01L 2300/0858* (2013.01); *B01L 2400/086* (2013.01)

(58) Field of Classification Search
CPC .................. B01L 3/502; B01L 3/5082; B01L 2300/0858; B01L 2400/086;
(Continued)

(56) References Cited

U.S. PATENT DOCUMENTS 4,755,300 A * 7/1988 Fischel .................. B01D 63/16
436/178
5,272,084 A * 12/1993 O'Connell ............. C12M 23/08
215/DIG. 3
(Continued)

FOREIGN PATENT DOCUMENTS

WO 2016183032 A1 11/2016
WO 2017025584 A1 2/2017

OTHER PUBLICATIONS

Gomez-Saurez et la., Analysis of bacterial detachment from substratum surfaces by the passage of air-liquid interfaces, Applied and Environmental Microbiology, 2001, vol. 67(6), pp. 2531-2537.
(Continued)

*Primary Examiner* — Benjamin R Whatley
*Assistant Examiner* — Jacqueline Brazin
(74) *Attorney, Agent, or Firm* — Bereskin & Parr LLP

(57) ABSTRACT

Surfaces contactable by a bulk liquid for use in particle isolation are described. The surfaces comprise a plurality of ribs spaced apart to capillarily retain a portion of the bulk liquid and particles of interest therebetween. Collectively, the portion of the bulk liquid retained by the plurality of ribs on the surface forms a liquid film. The one or more particles received within the space and enveloped by the liquid film may be protected from one or more forces exerted by a draining meniscus passing over the surface.

20 Claims, 11 Drawing Sheets

(58) Field of Classification Search
CPC ....... B01L 3/502746; B01L 2200/0668; B01L 2400/0406; C12M 47/02
USPC ............................................. 422/527
See application file for complete search history.

(56) References Cited

U.S. PATENT DOCUMENTS

| | | | | |
|---|---|---|---|---|
| 5,714,125 | A * | 2/1998 | Sagstetter | B01L 3/0293 600/583 |
| 2004/0209755 | A1 * | 10/2004 | Moore | B04B 5/0414 494/20 |
| 2006/0024824 | A1 | 2/2006 | Woodside et al. | |
| 2010/0067105 | A1 * | 3/2010 | Egeler | G01N 21/03 359/398 |
| 2013/0217010 | A1 | 8/2013 | Suchocki et al. | |

OTHER PUBLICATIONS

Noordmans et al., Detachment of polystyrene particles from collector surfaces by surface tension forces induced by air-bubble passage through a parallel plate flow chamber, Journal of Adhesion Science and Technology, 1997, vol. 11 (7), pp. 957-969, Abstract.

Sharma et al., Detachment of colloids from a solid surface by a moving air-water interface, Journal Colloid Interface Science, 2008, vol. 326(1), pp. 143-150, Abstract.

Lazouskaya et al., Colloid mobilization by fluid displacement fronts in channels, Journal of Colloid and Interface Science, 2013, vol. 406, pp. 44-50.

Andreev et al., Meniscus-Shear Particle Detachment in Foam-Based Cleaning of Silicon Wafers with an Immersion/Withdrawal Cell, Industrial & Engineering Chemistry Research, 2010, vol. 49(24), pp. 12461-12470, Abstract.

Suarez et al., Removal of colloidal particles from quartz collector surfaces as stimulated by the passage of liquid-air interfaces, Langmuir, 1999, vol. 15(15), pp. 5123-5127, Abstract.

Maleki et al., On the Landau-Levich transition, Langmuir, 2007, vol. 23(20), p. 10116-10122.

Maleki et al., Landau-Levich menisci, Journal of Colloid and Interface Science, 2011, vol. 354(1), pp. 359-363.

Mayer et al., Landau-Levich flow visualization: Revealing the flow topology responsible for the film thickening phenomena, Physics of Fluids, 2012, vol. 24(5), p. 052103:1-33.

Seiwert et al., Coating of a textured solid, Journal of Fluid Mechanics, 2011, vol. 669, p. 55-63.

Kao et al., Spinodal decomposition in particle-laden Landau-Levich flow, Physics of Fluids, 2012, vol. 24(4).

International Search Report and Written Opinion of corresponding International Patent Application No. PCT/CA2018/050615, pp. 8.

European Search Report of corresponding EP Application No. 18804997.7 dated Nov. 6, 2020, 8 pages.

* cited by examiner

DEVICES AND METHODS FOR SEPARATING PARTICLES FROM A LIQUID

RELATED APPLICATIONS

This application claims the benefit of U.S. Provisional Patent Application Ser. No. 62/511,503 filed May 26, 2017, the entire contents of which are hereby incorporated herein by reference for all purposes.

TECHNICAL FIELD

The present disclosure relates to the interaction of liquids and surfaces, and more specifically to the interaction of one or more particles in the liquid with the surface. The present disclosure also relates to the separation of particles, or a subset thereof, present in a liquid and brought into contact with the surface.

BACKGROUND

In many applications particles may be brought into contact with a surface in order to isolate them from a bulk liquid or from other particles present in the bulk liquid. Subsequent removal of the bulk liquid together with any contaminating particles may be an effective way to isolate and enrich for particles of interest. However, removing the bulk liquid away from the surface may impose certain forces on the particles in contact with the surface. Such forces may be damaging to the particles in contact with the surface or to the yield of isolated particles recovered from the bulk liquid.

Liquid-surface interactions dictate that a meniscus may form where a bulk liquid comes into contact with a surface at the gas-liquid-solid interface. A meniscus traversing a surface during draining or filling may exert certain forces, including friction, stiction, and shear forces, on particles at the gas-liquid-solid interface. A draining meniscus may thus exert net forces on particles in contact with the surface that displace said particles from the surface.

In the field of cell biology, the efficiency of separating one population of cells from a different population of cells or isolating a population of cells from a bulk liquid may be affected during the removal of the bulk liquid by pour-off or aspiration while the desired cell population is concentrated and retained at the surface, such as a container boundary, by selective forces. For example, magnetically labeled cells might be concentrated in a liquid film at the surface of the container by a magnet placed adjacent to the container. For the separation to be effective, magnetically-tagged cells should be retained at the surface during removal of the bulk liquid comprising cells without the magnetic tag and other contaminants.

Thus there remains a need for apparatuses and methods that may provide improved protection of particles in contact with a surface as a draining meniscus passes over the particles.

SUMMARY

The methods and apparatus disclosed herein provide for rib adapted surfaces and methods that may help reduce shear-off of particles at the surface under the influence of a draining meniscus of a bulk liquid. Such shear-off of particles may be reduced by the formation of a liquid film, through the capillary retention of a portion of the bulk liquid, within a space between a first rib and a second rib of the surface.

By way of non-limiting example, the disclosed methods and apparatus may improve the overall performance of both manual pour-off and automated pipetting methods of particle separation from a bulk liquid comprising a plurality of particles, in terms of (1) overall recovery values, (2) increased initial particle number range so that separation may be more effective at low particle numbers, (3) reduced variance in separation performance, (4) and faster separation times.

In a broad aspect, an apparatus for separating particles from a bulk liquid is provided. The apparatus includes a surface to be contacted by a particle-containing bulk liquid; a plurality of ribs on the surface, including at least a first rib and a second rib spaced apart from the first rib by a pitch distance; and a space between the first rib and the second rib dimensioned to capillarily retain therebetween a portion of the bulk liquid and at least a portion of the particles therein when the liquid contacting the surface is removed away from the surface.

In some embodiments, the first rib extends along a first longitudinal axis, and wherein the second rib extends along a second longitudinal axis.

In some embodiments, the second longitudinal axis is substantially parallel to the first longitudinal axis.

In some embodiments, the first longitudinal axis and the second longitudinal axis are generally linear.

In some embodiments, the first rib includes a first sidewall extending away from the surface and having a first base edge and a first protruding edge, and a second sidewall extending away from the surface and having a second base edge and a second protruding edge, the first base edge spaced apart from the second base edge by a first rib width and the first protruding edge connected to the second protruding edge at a first apex height, and the second rib includes a third sidewall extending away from the surface and having a third base edge and a third protruding edge, and a fourth sidewall extending away from the surface and having a fourth base edge a fourth protruding edge, the third base edge spaced apart from the fourth base edge by a second rib width and the third protruding edge connected to the fourth protruding edge at a second apex height.

In some embodiments, the first apex height and the second apex height are each between about 20 um to about 1 mm.

In some embodiments, the apparatus also includes a third rib spaced apart from the second rib by the pitch distance, the third rib including a fifth sidewall extending away from the surface and having a fifth base edge and a fifth protruding edge, and a sixth sidewall extending away from the surface and having a sixth base edge and a sixth protruding edge, the fifth base edge spaced apart from the sixth base edge by a third rib width and the fifth protruding edge connected to the sixth protruding edge at a third apex height.

In some embodiments, the third apex height is between about 20 um and about 1 mm and is different than the first and second apex heights.

In some embodiments, the first protruding edge is connected to the second protruding edge by a first top wall, and the third protruding edge is connected to the fourth protruding edge by a second top wall.

In some embodiments, the fifth protruding edge is connected to the sixth protruding edge by a third top wall In some embodiments, a width of the first top wall, the second top wall and the third top wall is between about 1 um and about 1 mm.

In some embodiments, the pitch distance is at least 1 um.

In some embodiments, the pitch distance is less than about 1 mm.

In some embodiments, the pitch distance between adjacent ones of the plurality of ribs is uniform.

In some embodiments, the first rib has a first cross-sectional shape taken in a plane orthogonal to the first longitudinal axis and the second rib has a second cross-sectional shape taken in the plane.

In some embodiments, the first cross-sectional shape is the same as the second cross-sectional shape.

In some embodiments, the first cross-sectional shape is a quadrilateral.

In some embodiments, the first cross-sectional shape is a triangle.

In some embodiments, the first and second longitudinal axes are oriented relative to a flow direction of the bulk liquid thereover such that the first and second longitudinal axes not parallel to the flow direction.

In some embodiments, the surface comprises an inner surface of a container.

In some embodiments, the first top wall and the second top wall are coplanar with the inner surface of the container.

In some embodiments, the container is a tube.

In some embodiments, the first and second ribs extend a rib length along a surface longitudinal axis, and wherein the rib length is between 5% and 95% of the surface longitudinal axis.

In a broad aspect, a container for holding a particle-containing bulk liquid is provided. The container includes a closed bottom end having a bottom wall, an open upper end, one or more sidewalls extending from the bottom wall to the upper end and an inner surface bounding an interior of the container and an opposed outer surface; a plurality of ribs on the inner surface and extending away from the inner surface into the interior of the container, the plurality of ribs including at least a first rib and a second rib spaced apart from the first rib by a pitch distance; and a space between the first rib and the second rib; whereby when bulk liquid is contained in the interior of the container the bulk liquid contacts the inner surface, the first and second ribs, and the space between the first and second ribs, and whereby the first and second ribs are dimensioned to capillarily-retain therebetween a portion of the bulk liquid and at least a portion of the particles therein when the bulk liquid contacting the surface is removed away from the surface.

In some embodiments, the sidewall extends along a container axis from the bottom end to the upper end, and wherein the first rib extends along a first rib axis that is parallel to the container axis.

In some embodiments, the plurality of ribs cover between 5% and 95% of an area of the inner surface of the sidewall.

In some embodiments, the plurality of ribs are located at a bottom end, a midpoint, or the upper end of the container.

In some embodiments, the sidewall comprises the plurality of ribs.

In some embodiments, the plurality of ribs are integrally formed with the container sidewall.

In a broad aspect, a method for separating particles from a bulk liquid using an apparatus comprising a surface, a plurality of ribs on the surface, including at least a first rib and a second rib spaced apart from the first rib by a pitch distance, and a space between the first rib and the second rib is provided. The method includes contacting the apparatus with the bulk liquid, whereby the bulk liquid contacts the surface, the first and second ribs, and the space between the first and second ribs; receiving at least a first portion of the particles in the bulk liquid into the space between the first and second ribs; removing the bulk liquid away from the surface, a portion of the bulk liquid capillarily-retained between the first and second ribs to form a liquid film therebetween; shielding the particles received between the first and second ribs and entrained in the liquid film from one or more forces of a draining meniscus as the bulk liquid is removed away from the surface; and resuspending in a buffer the shielded particles entrained within the liquid film.

In some embodiments, the method also includes applying a first force to urge the particles into the space between the first and second ribs.

In some embodiments, at least a second portion of the particles urged into the space are responsive to the first force.

In some embodiments, the first force is a magnetic attraction force and the responsive particles have a first magnetic charge attracted to a magnet, such that the apparatus is between the magnet and the bulk liquid whereby the first force urges the first portion of the particles toward the space.

In some embodiments, the particles received into the space evacuate the space in the absence of the first force.

In some embodiments, the method also includes adding a diamagnetic additive to the bulk liquid.

In some embodiments, the diamagnetic additive is gadolinium.

Other features and advantages of the present disclosure will become apparent from the following drawings and detailed description. It should be understood, however, that the detailed description and the specific examples while indicating preferred embodiments of the disclosure, are given by way of illustration only, since various changes and modifications within the spirit and scope of the disclosure will become apparent to those skilled in the art from this detailed description.

BRIEF DESCRIPTION OF DRAWINGS AND FIGURES

The disclosure will now be described in relation to the drawings in which.

FIG. 6B shows a perspective view photographs depicting the shear effect of particles/cells from a sidewall of a container as a draining meniscus traverses thereover. Herein, PMBCs were positively selected using anti-CD45 magnetically-tagged antibodies. The tube was placed in a STEM-CELL Silver magnet for 10 minutes, capped, the magnet was tipped to the horizontal, and the tube pulled out carefully to take the image.

Figure 7:
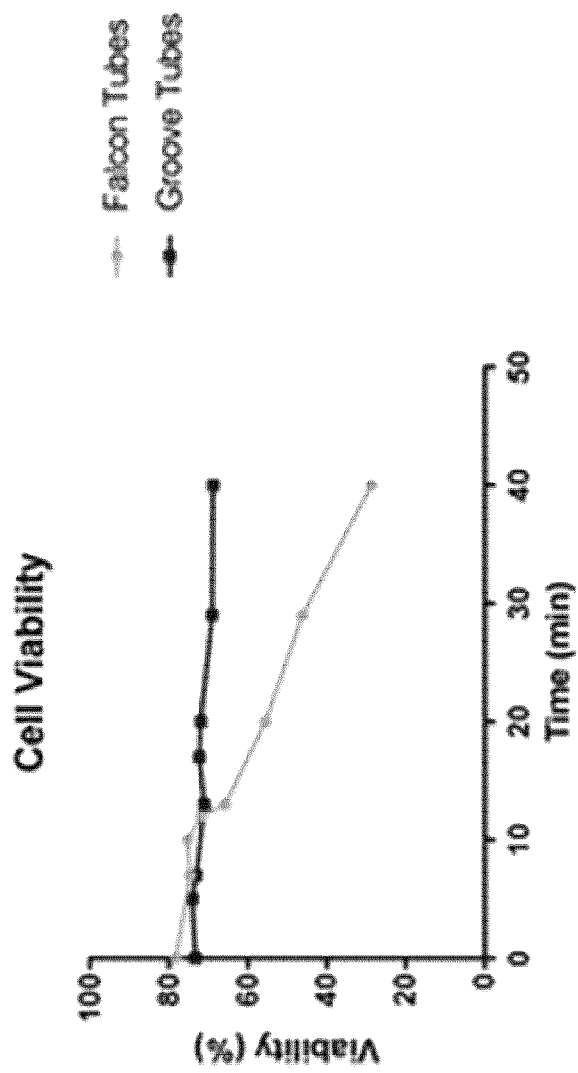

FIG. 7 shows a diagram showing improved viability of separated cells retained in G-tubes (Groove Tubes) vs. F-tubes (Falcon Tubes) after the bulk fluid has been removed.

Figure 8:
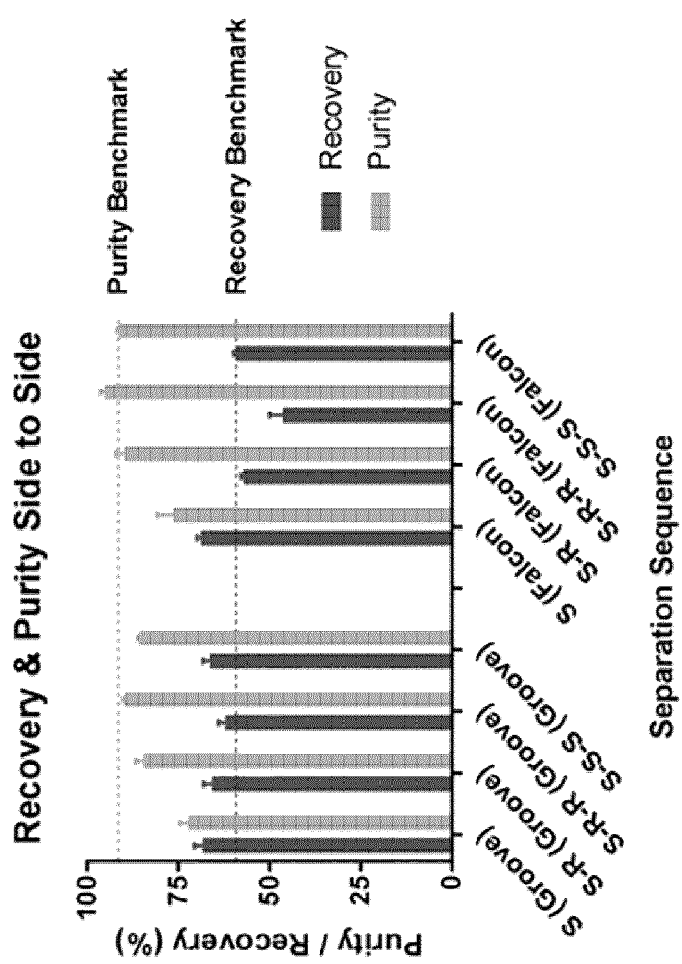

FIG. 8 shows a diagram assessing purity and recoveries of cells separated using G-tubes (Groove) and F-tubes (Falcon) under various separation procedures. "S" represents a separation step which includes a wash step intended to remove a majority of separated cells and/or particles from the surface, and "R" represents a rinse step not intended to remove a majority of separated cells and/or particles from the surface.

FIG. 9A shows a perspective sectional view of a tube comprising a plurality of ribs on an inner sidewall thereof (G-Tube), according to one embodiment.

FIG. 9B shows enlargements (i) and (ii) of the boxed regions shown in FIG. 9A.

FIG. 9C shows a perspective view of the exemplary tube depicted in FIG. 9A comprising a pipette seat at a closed bottom end thereof.

Figure 10:
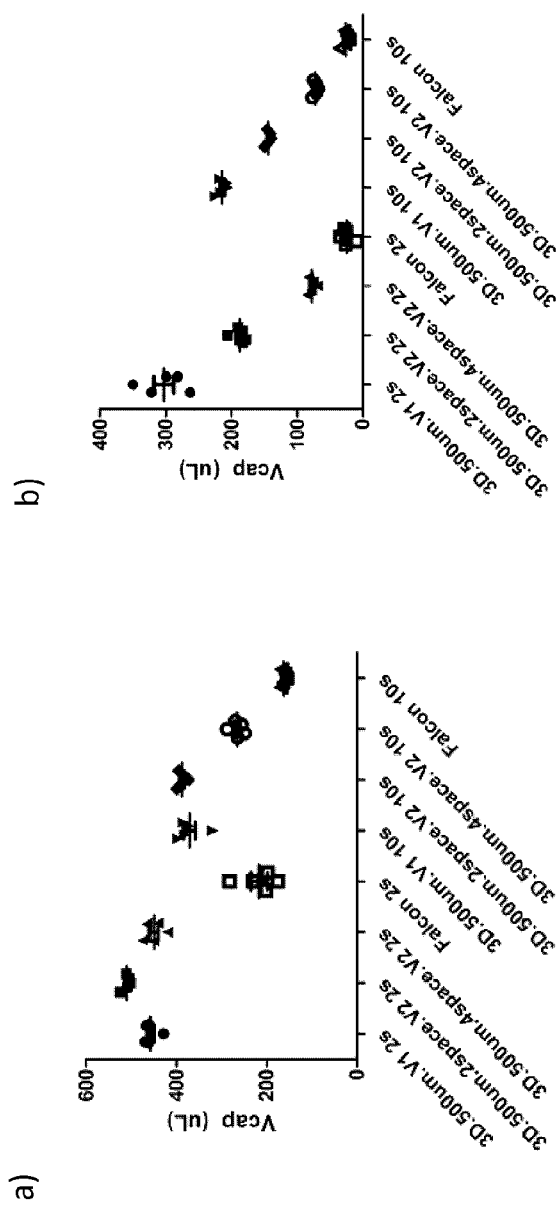

FIG. 10A shows a diagram showing the liquid film volume retained in G-Tubes and F-tubes during pour-off cell separation methods. The plot shows results for EasySep cell separation methods using G-Tubes and F-Tubes comprising different rib densities on the surface. The 2-space and 4-space tubes refer to tubes having ½ and ¼ of the rib density, respectively.

FIG. 10B shows a diagram showing the liquid film volume retained in G-Tubes and F-tubes during aspiration cell separation methods. The plot shows results for RoboSep cell separation methods using G-Tubes and F-Tubes comprising different rib densities on the surface (as in FIG. 8A)).

Figure 11:
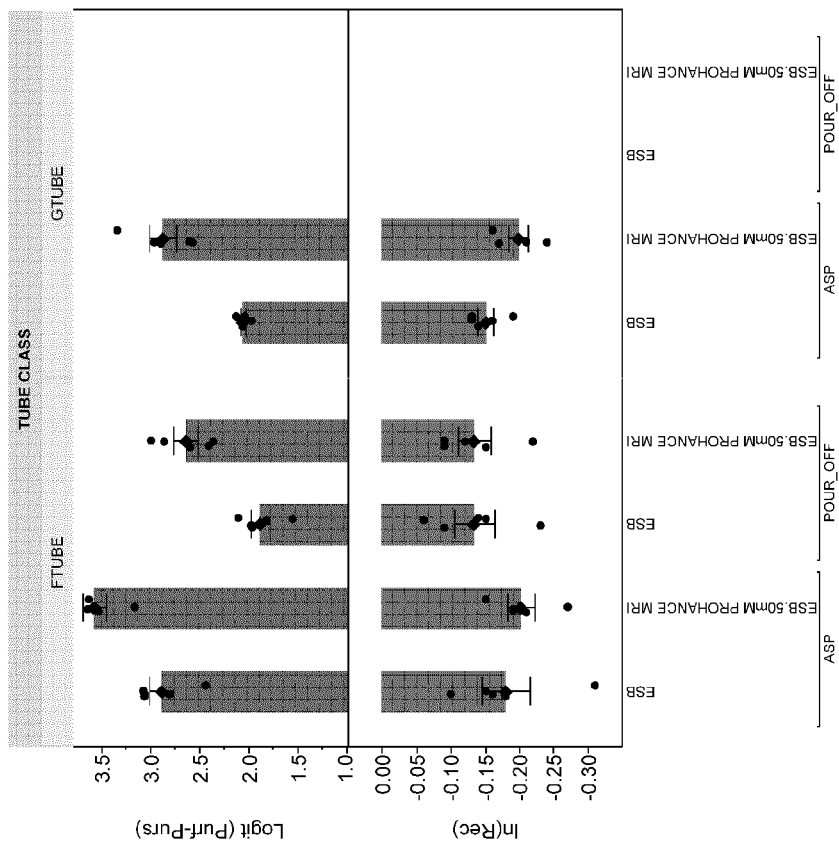

FIG. 11 shows a diagram showing the effect on recovery and purity of a diamagnetic additive in aspiration or pour-off methods of cell separation using G-Tubes and F-Tubes.

DETAILED DESCRIPTION

The rib-adapted surfaces described herein may be used in combination with a bulk liquid comprising one or more populations of particles. The plurality of ribs may help to shield at least a portion of the particles of the population(s) in contact with the surface from certain forces exerted by a draining meniscus traversing thereover.

The particles of this disclosure may be any biological or non-biological particles. Biological particles may include but are not limited to: cells, whether prokaryotic or eukaryotic, and aggregates thereof; subcellular components, such as organelles or extracellular vesicles; proteins; nucleic acids; or prions. Non-biological particles may include but are not limited to: a particle comprising one or more metals and/or metalloids, or any other inorganic matter; or a particle comprising organic matter. In certain embodiments, the particles may be a combination of a biological particle and non-biological particle. For example, the particles of the disclosure may comprise a cell complexed with one or more magnetic or magnetizable particles. The particles of this disclosure may range in mean diameter from the Angstrom level to millimeters.

Surfaces

Apparatus for separating particles from a bulk liquid 1 comprises a surface 10. The surface may consist of or comprise any material that may be contacted by a particle-containing bulk liquid 13. Exemplary surfaces may comprise glass, a polymer or polymers, metal, or metalloids. In one embodiment, surface 10 may be substantially planar (FIG. 1a). In another embodiment, surface 10 may comprise an inner sidewall or an inner surface of a container, including but not limited to a tube, such as a closed-bottom tube, a flask, a bottle, or other vessel (FIG. 1b-e). In any case, the substantially planar surface or the inner sidewall or inner surface of the container may be contacted by a liquid, including a particle-containing bulk liquid 13.

Ribs

Figure 1:
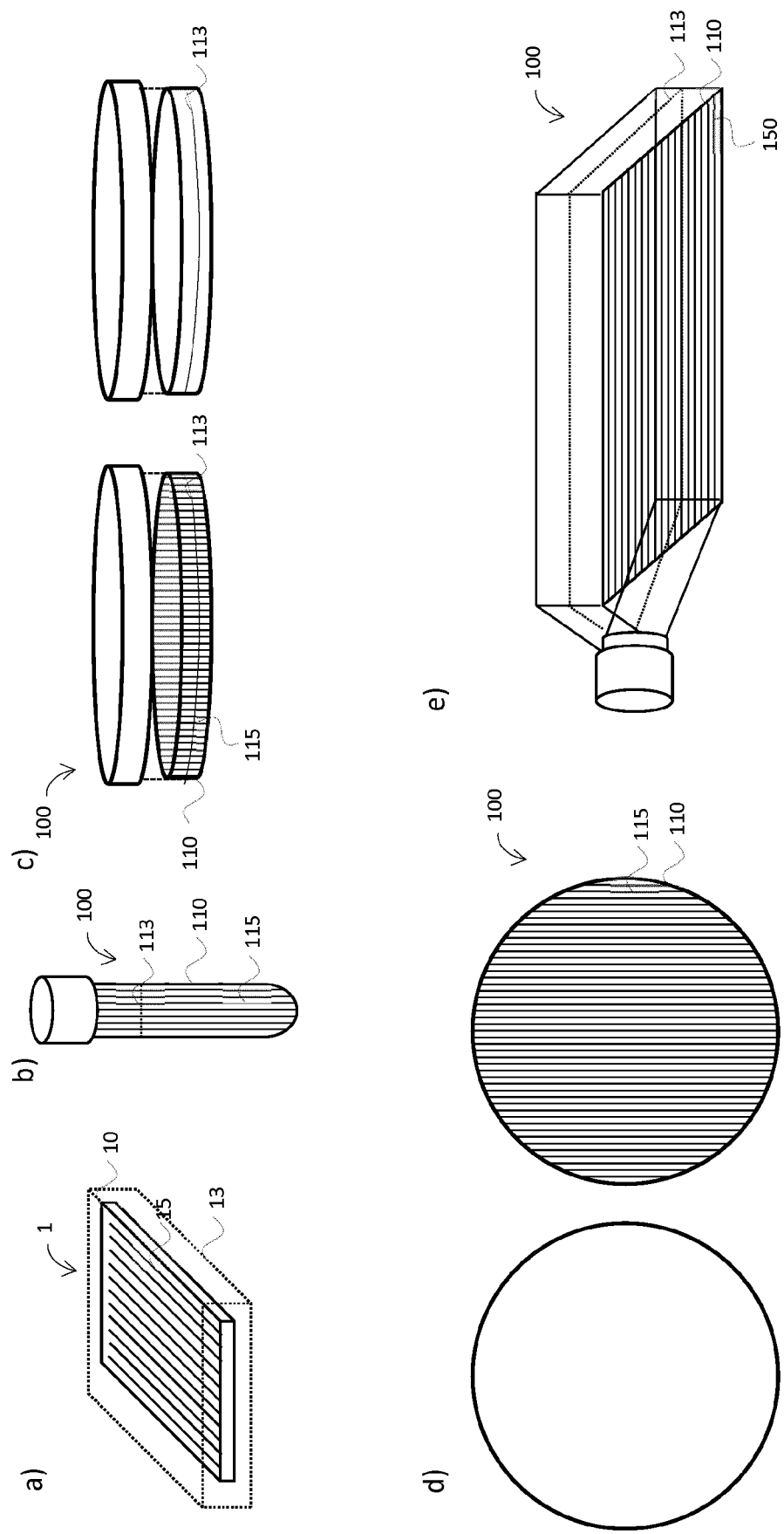
FIG. 1A shows a perspective view of an apparatus for separating particles from a bulk liquid according to one embodiment, the apparatus having a substantially planar surface comprising a plurality of ribs.
FIG. 1B shows a perspective view of an apparatus for separating particles from a bulk liquid according to another embodiment, the apparatus shaped as a tube comprising a plurality of ribs on a surface thereof.
FIG. 1C shows an exploded view of two apparatuses for separating particles from a bulk liquid according to another embodiment, the apparatuses shaped as circular culture containers comprising a plurality of ribs on a surface thereof.
FIG. 1D shows bottom views of the culture dishes of FIG. 1C.
FIG. 1E shows a perspective view of an apparatus for separating particles from a bulk liquid according to another embodiment, the apparatus shaped as a rectangular culture container comprising a plurality of ribs on a surface thereof.
Figure 2:
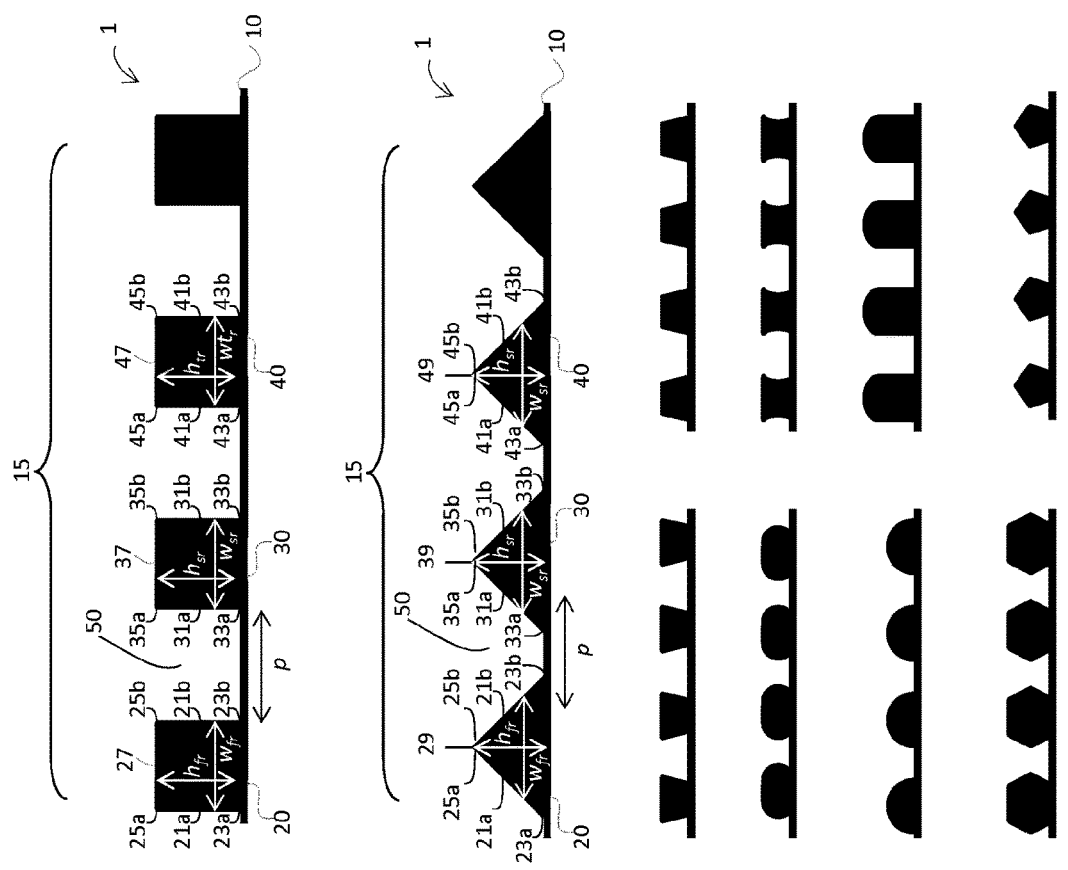
FIG. 2 shows cross-sectional views of exemplary surfaces of the apparatuses of FIG. 1 comprising a plurality ribs.

Apparatus 1 comprises a plurality of ribs 15 on surface 10 (FIG. 1). Plurality of ribs 15 include at least a first rib 20 and a second rib 30 (FIG. 2). Each of first rib 20 and second rib 30 extend along respective first and second longitudinal axes. In one embodiment the second longitudinal axis is substantially parallel to the first longitudinal axis. In other embodiments first longitudinal axis and second longitudinal axis are generally linear. In specific embodiments the first and second longitudinal axes may not be generally linear. In such embodiments the first and second longitudinal axes may include a serpentine, helical, or zig-zagged pattern.

As shown in FIG. 2, first rib 20 may include a first sidewall 21a extending away from surface 10 and having a first base edge 23a and a first protruding edge 25a. First rib 20 may also include a second sidewall 21b extending away from surface 10 and having a second base edge 23b and a second protruding edge 25b. Also as shown in FIG. 2, second rib 30 may include a third sidewall 31a extending away from surface 10 and having a third base edge 33a and a third protruding edge 35a. Second rib 30 may also include a fourth sidewall 31b extending away from surface 10 and having a fourth base edge 33b and a fourth protruding edge 35b.

In some embodiments, first base edge 23a may be spaced apart from second base edge 23b by a first rib width $w_{fr}$. Similarly, third base edge 33a may be spaced apart from fourth base edge 33b by a second rib width $w_{sr}$. In such embodiments, first rib width $w_{fr}$ and/or second rib width $w_{sr}$ may be between 1 um and about 1 mm, or larger.

In other embodiments first sidewall 21a and second sidewall 21b, and/or third sidewall 31a and fourth sidewall 31b, may extend and diverge from substantially a common point on surface 10, such as when first rib 20 and/or second rib 30 may assume an inverted triangular cross-sectional shape orthogonal to the first longitudinal axis of first rib 20 and second longitudinal axis of second rib 30, respectively. In such other embodiments, first base edge 23a and second base edge 23b may substantially overlap with each other, and/or third base edge 33a and fourth base edge 33b may also substantially overlap with each other. Accordingly, first rib width $w_{fr}$ and/or second rib width $w_{sr}$ may more appropriately be taken across first and second sidewalls 21a and 21b and/or third and fourth sidewalls 31a and 31b, respectively, at a position spaced away from surface 10.

First protruding edge 25a may be connected to second protruding edge 25b at a first rib apex height $h_{fr}$, and third protruding edge 35a may be connected to fourth protruding edge 35b at a second rib apex height $h_{sr}$. In some embodiments, first protruding edge 25a and second protruding edge 25b may be connected by a first top wall 27, and/or third protruding edge 35a and fourth protruding edge 35b may be connected by a second top wall 37. In other embodiments, first protruding edge 25a may be directly connected to second protruding edge 25b, and/or third protruding edge 35a may be directly connected to fourth protruding edge 35b, for example with respective ribs having a triangular or pointed cross-sectional shape orthogonal to a first longitudinal axis of first rib 20 and/or second longitudinal axis of second rib 30, respectively.

In embodiments where first rib 20 and/or second rib 30 have a cross-sectional shape taken in a plane orthogonal to first longitudinal axis and second longitudinal axis, respectively, that is arcuate or rounded, the protruding edges of respective sidewalls of a rib may meet at the rib apex height.

In another embodiment, apparatus 1 may further comprise a third rib 40. Third rib 40 may include a fifth sidewall 41a extending away from surface 10 and having a fifth base edge 43a and a fifth protruding edge 45a. Third rib 40 may also include a sixth sidewall 41b extending away from surface 10 and having a sixth base edge 43b and a sixth protruding edge 45b. In some embodiments, fifth base edge 43a may be spaced apart from sixth base edge 43b by a third rib width $w_{tr}$. In such embodiments, third rib width $w_{tr}$ may be may be between 1 um and about 1 mm, or larger. In other embodiments, fifth sidewall 41a and sixth sidewall 41b may extend and diverge from substantially a common point on surface 10, such as when third rib 40 may assume an inverted triangular cross-sectional shape orthogonal to a third longitudinal axis of third rib 40. In such other embodiments, fifth base edge 43a and sixth base edge 43b may substantially overlap with each other. Accordingly, third rib width $w_{tr}$ may more appropriately be taken across fifth and sixth sidewalls 41a and 41b at a position spaced away from surface 10.

Fifth protruding edge 45a may be connected to sixth protruding edge 45b at a third rib apex height $h_{tr}$. In some embodiments, fifth protruding edge 45a and sixth protruding edge 45b may be connected by a third top wall 47. In other embodiments, fifth protruding edge 45a may be directly connected to sixth protruding edge 45b, for example with third rib 40 having a triangular or pointed cross-sectional shape orthogonal to the third longitudinal axis of third rib 40. In certain embodiments, a width of the first top wall 27, the second top wall 37, and the third top wall 47 may be between about between 1 um and about 1 mm, or larger.

In some embodiments, first rib apex height $h_{fr}$ (taken for example at first top wall 27), second rib apex height $h_{sr}$ (taken for example at second top wall 37), and/or third apex rib height $h_{tr}$ (taken for example at third top wall 47) may be between 20 um to about 1 mm measured in a direction orthogonal to and extending away from surface 10. In certain embodiments, first rib apex height $h_{fr}$ and second rib apex height $h_{sr}$ may each be between about 20 um to about 1 mm. In other embodiments, first rib apex height $h_{fr}$ and second rib apex height $h_{sr}$ may be the same. In still other embodiments, third apex rib height $h_{tr}$ may be between about 20 um to about 1 mm and may be different than the first and second apex heights, respectively.

Third rib 40 may be spaced apart from second rib 30, and second rib 30 may be spaced apart from first rib 20 by a pitch distance p (FIG. 2). Pitch distance p may be measured in a plane substantially parallel to surface 10 and between adjacent ribs, for example, between second sidewall 21b and third sidewall 31a. Pitch distance p may be measured at any point between adjacent ribs, for example at any point along adjacent sidewalls of adjacent ribs. Depending on the cross-sectional geometries (taken in a plane orthogonal to the longitudinal axes of adjacent ribs), pitch distance p may be measured between, for example, second base edge 23b and third base edge 33a. In the alternative, pitch distance p may be measured between, for example, second protruding edge 25b and third protruding edge 35a. Generally, pitch distance p should be sufficient to receive at least one diameter of a particle of interest. For example, most animal cells may have a diameter of about 10 to 30 um, and certain larger animal cells such as megakaryocytes may have a diameter of about 160 um. Further, many viruses may have a diameter of about 30 nm to about 250 nm, or larger. Still further, many bacteria may have a diameter of about 100 nm to about 10,000 nm, or larger. In some embodiments, pitch distance p may be at least 10 um. In other embodiments pitch distance p may be less than 1 mm.

In some embodiments, pitch distance p between adjacent ones of the plurality of ribs 15 may be uniform. In other embodiments, pitch distance p between adjacent ones of the plurality of ribs 15 may not be uniform. In embodiments, where pitch distance is not uniform, pitch distance may alternate between a relatively larger pitch distance and a relatively smaller pitch distance.

Each sidewall of a respective rib of plurality of ribs 15 may form a defined edge with surface 10. In the embodiments shown in FIG. 2, the edge formed between each sidewall of a respective rib with surface 10 may be influenced by the cross-sectional shape of the plurality of ribs 15 taken in a plane orthogonal to the longitudinal axes thereof. The cross-sectional shape of the plurality of ribs 15 may be any polygon, or portion thereof. In some embodiments, first rib 20 has a first cross-sectional shape taken in a plane orthogonal to the first longitudinal axis and second rib 30 has a second cross-sectional shape taken in the plane.

While reference may be made in the following discussion to first rib 20 the same discussion may be applicable to second rib 30 and/or third rib 40. In some embodiments, first rib 20 may comprise generally planar sidewalls 21a and 21b, generally parallel to each other, and intersecting surface 10 at an angle of between 80° to 100° (FIG. 2). In certain embodiments, sidewalls 21a and 21b may intersect surface 10 at an angle of approximately 90°, or 90°. In some embodiments, first cross-sectional shape is substantially square or rectangular, or is a quadrilateral, such as a trapezoid. In still other embodiments, the first cross-sectional shape is curved, whether inwardly or outwardly, and comprising a first top wall (FIG. 2).

In other embodiments, the first cross-sectional shape is a triangle (FIG. 2). In embodiments where the first cross-sectional shape is a triangle, first sidewall and second sidewall may intersect surface 10 at angles of 60° to form an equilateral triangle. In still other embodiments where the first cross-sectional shape is a triangle, first sidewall and second sidewall may intersect surface 10 to form an isosceles triangle. Or, the first cross-sectional shape may be arcuate or hemi-spherical (FIG. 2).

In still other embodiments, first cross-sectional shape may compound various shapes, for example, first cross-sectional shape comprises a quadrilateral and having an arcuate or pointed top wall (FIG. 2). Such cross-sectional shapes may be appropriate where the particles may come into contact with and settle on a top wall of plurality of ribs 15, such as first top wall 27 or second top wall 37, rather than in space 50 between first rib 20 and a second rib 30. Without being limited by the foregoing, any shape that may urge particles into space 50 and away from the top wall of one or more of the plurality of ribs 15 may be encompassed by the present disclosure. In such embodiments, first rib 20 may comprise a first apex 29 and second rib may comprise a second apex 39 that is approximately the width of a particle which may come into contact therewith. Or, first apex 29 and second apex 39 may have a width less than the width of a particle which may come into contact therewith.

In some embodiments first cross-sectional shape is the same as the second cross-sectional shape. In other embodiments, first cross-sectional shape is different from second cross-sectional shape.

Figure 3:
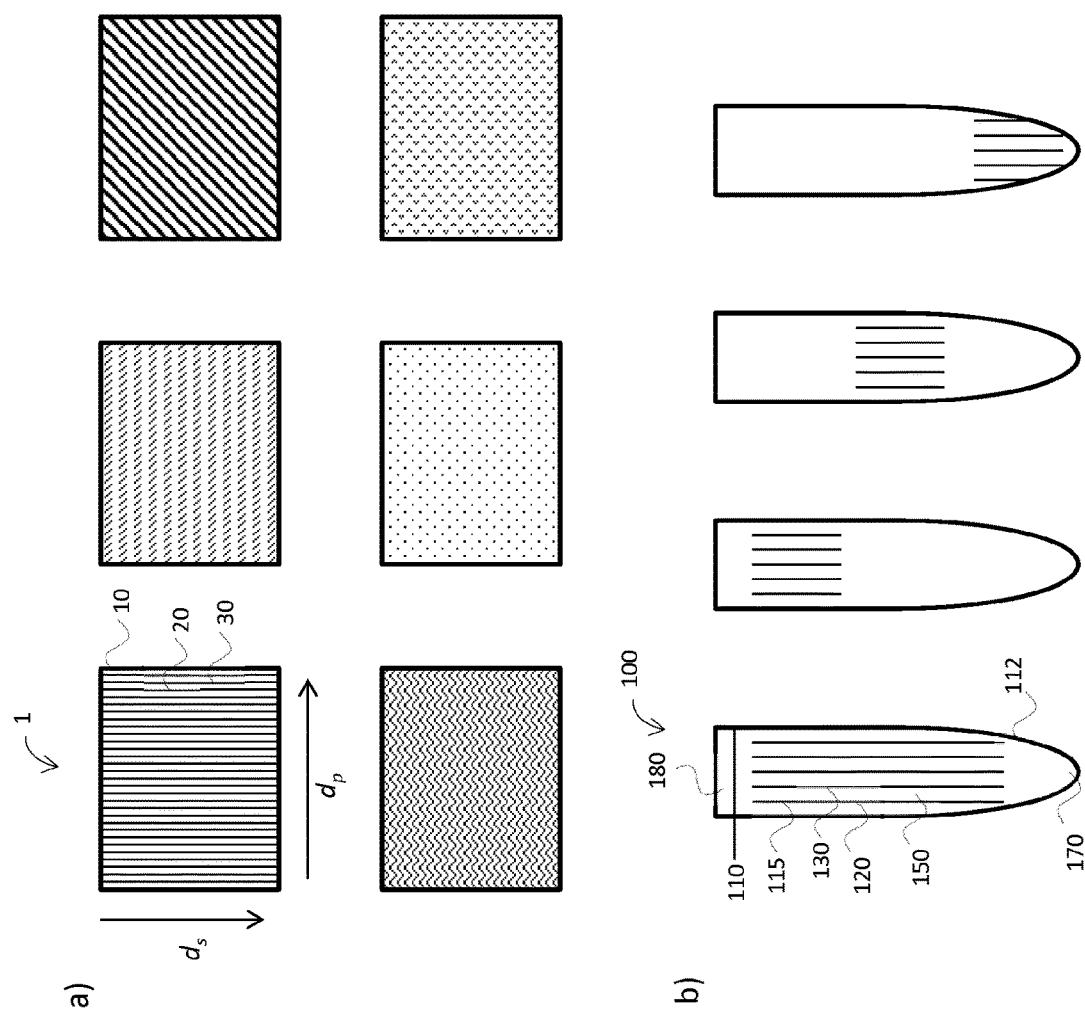
FIG. 3A shows top views of exemplary surfaces of the apparatuses of FIG. 1 having various rib patterns. The shown surfaces comprising a plurality of ribs may represent either a substantially planar surface or a portion of a non-planar surface.
FIG. 3B shows front views of a laboratory tube comprising a plurality of ribs on an inner sidewall thereof. The ribs on the inner surface thereof may be patterned as depicted in FIG. 3A.

Plurality of ribs 15 may be oriented in any way provided such orientation may capillarily retain a portion of the bulk liquid following drainage thereof away from surface 10 (FIG. 3a). In a preferred embodiment plurality of ribs 15 may be generally linearly disposed in the same direction $d_s$ in which a draining meniscus passes over surface 10, wherein the first and second longitudinal axes (of first rib 20 and second rib 30, respectively) are oriented relative to a flow direction of the bulk liquid thereover such that the first and second longitudinal axes are parallel to the flow direction. While in other embodiments plurality of ribs 15 may extend horizontally $d_p$, or substantially perpendicularly, and generally linearly with respect to the direction in which a draining meniscus passes over surface 10. In a particular embodiment, the first and second longitudinal axes (of first rib 20 and second rib 30, respectively) are oriented relative to a flow direction of the bulk liquid thereover such that the first and second longitudinal axes are not parallel to the flow direction. In still other embodiments, the ribs may be serpentine, helical, hatched or otherwise patterned, and extend along a longitudinal axis in any direction along the surface relative to the flow direction of the draining meniscus. Indeed, it is only relevant that the orientation of the ribs may be effective for capillarily retaining a portion of a bulk liquid as a draining meniscus passes over the surface.

In an embodiment of a container 100 for holding a particle-containing bulk liquid 113, the container may be a tube, a flask, a dish, or the like. In some embodiments, the container may comprise a closed bottom end having a bottom wall, an open upper end, one or more sidewalls extending from the bottom wall to the upper end and an inner surface bounding an interior of the container and an opposed outer surface. In a particular embodiment, the container 100 is a tube (FIG. 3b). Container 100 comprises a plurality of ribs 115 (aspects of which are inclusively described above) on an inner surface 110 thereof. Plurality of ribs 115 may extend away from inner surface 110 into the interior of container 100. As indicated above, plurality of ribs 115 include at least a first rib 120 and a second rib 130. Also as indicated above, second rib 130 may be spaced apart from first rib 120 by a pitch distance (not shown in FIG. 3b; see FIG. 2); the pitch distance defining a space 150 between first rib 120 and second rib 130.

In a particular embodiment, sidewall 112 extends along a container axis from the bottom end 170 to the top end 180. Inner surface 110 of sidewall 112 includes first rib 120 extending along a first rib axis that is parallel to the container axis. The plurality of ribs 115 may cover between 5% and 95% of an area of the inner surface 110 of the sidewall 112. In some embodiments, the inner surface 110 and/or the sidewall 112 may comprise the plurality of ribs 115 extending from substantially near the closed bottom end 170 of container 100 to substantially near the open upper end 180 of container 100.

In other embodiments, the ribs may not extend substantially the entire length of the container. For example, only part of inner surface 110 may comprise the plurality of ribs 115. In one embodiment, the plurality of ribs 115 may be substantially located at bottom end 170 of container 100, such as where a pellet of particles may form under a gravitational force, including but not limited to a centrifugal force. In another embodiment, the plurality of ribs 115 may be substantially located at upper end 180 of container 100. In a still further embodiment, the plurality of ribs 115 may be substantially located at a midpoint of the container 100. The skilled person will further appreciate that the plurality of ribs need not be located around the entire circumference of the sidewall and/or inner surface of the container.

Ribs may also be provided on the surface at densities suited for particular downstream applications. The density of ribs may be established by providing a desired number of the plurality of ribs 15 or 115 on a unit measurement of surface 10 or 110, respectively. As an illustrative example, ten ribs having a width of 1 mm may be desired across a 20 mm measurement of a surface. Such a configuration may yield a density of 1 rib per 2 mm measurement of the surface (in the appropriate direction). Notwithstanding, any density of ribs provided on the surface may be encompassed by this disclosure, whereby the desired density may be limited by factors such as the practicality of forming ribs on the surface or the ability to capillarily retain a portion of a bulk liquid traversing the rib-adapted surface.

Still further, surfaces adapted with a plurality of ribs may be prepared in any way known in the art. Surfaces may be manufactured using injection-molding to form a plurality of ribs thereon. Or, surfaces comprising ribs may be 3D-printed using any variety of substrate processable by a 3D-printer. Or, a substantially smooth surface may be adapted with a plurality of ribs by adhering individual ribs thereon. In the alternative, a substantially smooth surface may be adapted with ribs by adhering to the surface a plurality of ribs disposed on a common backing. Still further, surfaces may be physically adapted with a plurality of ribs after the surface is manufactured for example by manual or mechanical scoring or etching. Or, surfaces may be chemically adapted with a plurality of ribs by applying a suitable composition thereto.

Spaces

Apparatus 1 or container 100 further comprises a space 50 between first rib 20 and second rib 30, or a space 150 between first rib 120 and second rib 130, respectively. While the discussion that follows may focus on apparatus 1 and space 50, it may equally apply to container 100 and space 150.

Figure 4:
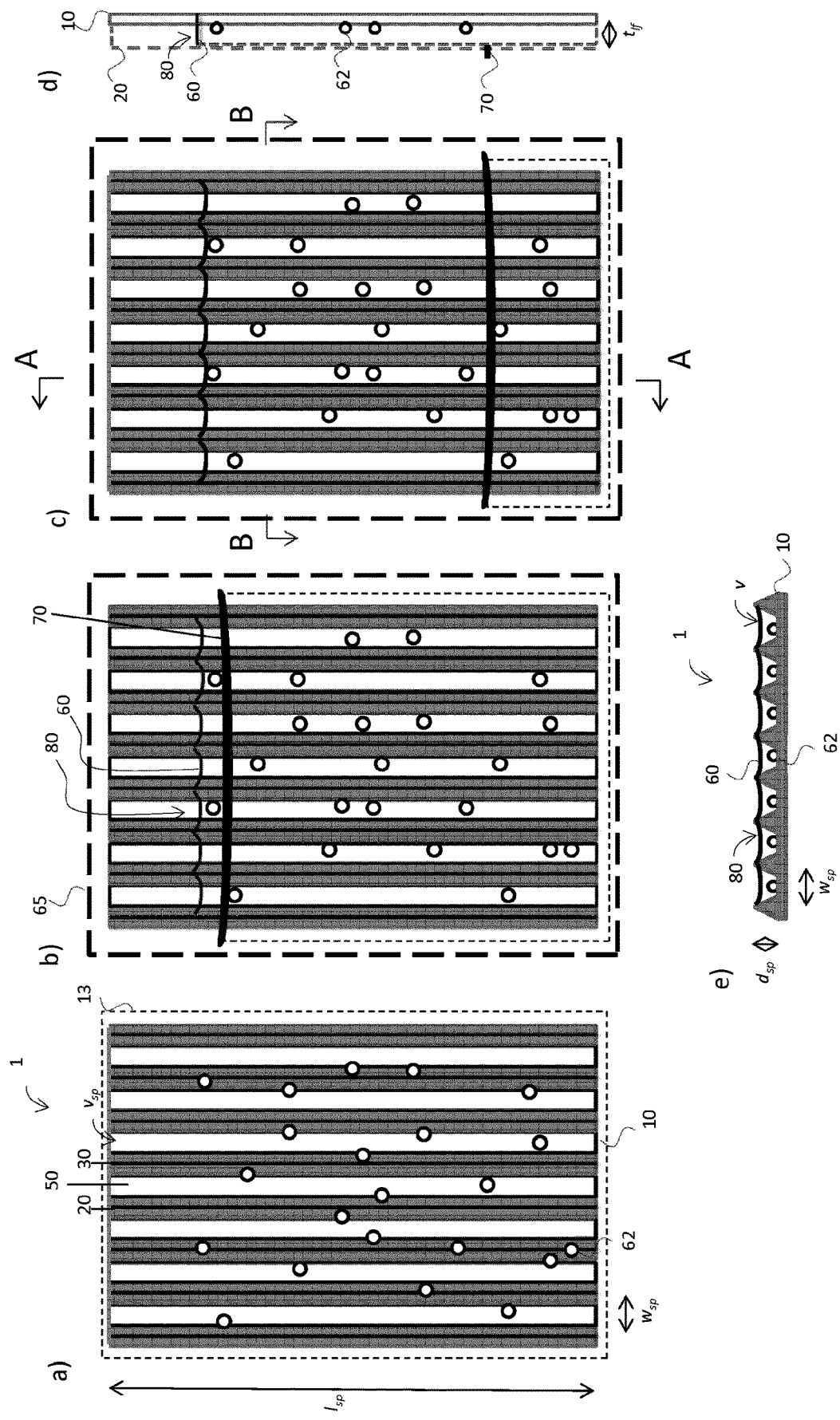
FIG. 4A shows an orthographic top/front view of a surface comprising a plurality of ribs having been contacted by a particle-containing bulk liquid.
FIG. 4B shows an orthographic top/front view of the surface of FIG. 4A after at least a portion of the particles in the bulk liquid have been exposed to a first force and removal of the bulk liquid away from the surface has been initiated.
FIG. 4C shows an orthographic top/front view of the surface of FIG. 4B once substantially all of the bulk liquid has been removed away from the surface.
FIG. 4D shows a side view through line A of the surface of FIG. 4C.
FIG. 4E shows an orthographic front/top view through line B of the surface of FIG. 4C.

Space 50 is dimensioned to capillarily retain between first rib 20 and second rib 30 a portion 60 of bulk liquid 13 and at least a portion of the particles 62 therein when the bulk liquid 13 contacting surface 10 is removed away from the surface (see for example FIG. 4b or FIG. 4c). Capillary retention of a portion of the bulk liquid within a space may be influenced by many factors. Such factors include but are not limited to the contact angle between the bulk liquid and the surface, the viscosity of the bulk liquid, the volume of the space, and the distribution of hydrophobic and hydrophilic domains on the surface.

A volume $v_{sp}$ of space 50, and by extension portion 60 of bulk liquid 13 capillarily retained between first rib 20 and second rib 30, may be an important consideration in applications using apparatus 1 or container 100. The volume $v_{sp}$ of space 50 is a function of the width $w_{sp}$ of space 50, a depth $d_{sp}$ of space 50, and a length $l_{sp}$ of space 50. For example, a space having an appropriately small volume may be necessary when the bulk liquid is characterized by a low density. As another example, if the bulk liquid comprises a density comparable to liquid water, the space between ribs may be on the order of several hundred microns to a few millimeters.

Furthermore, volume v of space 50 may be dimensioned to accommodate at least one particle 62, as measured by a particle diameter, to be received within the space, such as under the influence of a first force 65 (such as a magnetic field provided by a magnet). In some instances submicron particles may be collected within the space between the first rib 20 and second rib 30, such as virus particles or bacteria. In other instances micron sized cells may be collected within the space 50 between the first rib 20 and second rib 30. In other instances particles of several hundred microns, such as mammalian cell aggregates, may be collected within the space 50 between the first rib 20 and the second rib 30.

The portion 60 of bulk liquid 13, and the portion of particles 62 therein, capillarily retained within space 50 should be exposed to a reduced liquid velocity as a draining meniscus 70 passes over surface 10. In such circumstance, the one or more forces of draining meniscus 70 may be reduced vis-à-vis the capillarily retained portion 60 of bulk liquid 13, thereby shielding the portion of particles 62 received into the space between the first rib 20 and the second rib 30 and entrained in the portion 60 of bulk liquid 13.

Liquid Film

Collectively or individually, the capillarily-retained portion 60 of bulk liquid 13 within space 50 between the plurality of ribs 15 may form a liquid film 80. In the collective sense, liquid film 80 may cover surface 10 after bulk liquid 13 has been removed away from the surface (FIG. 4e).

Figure 5:
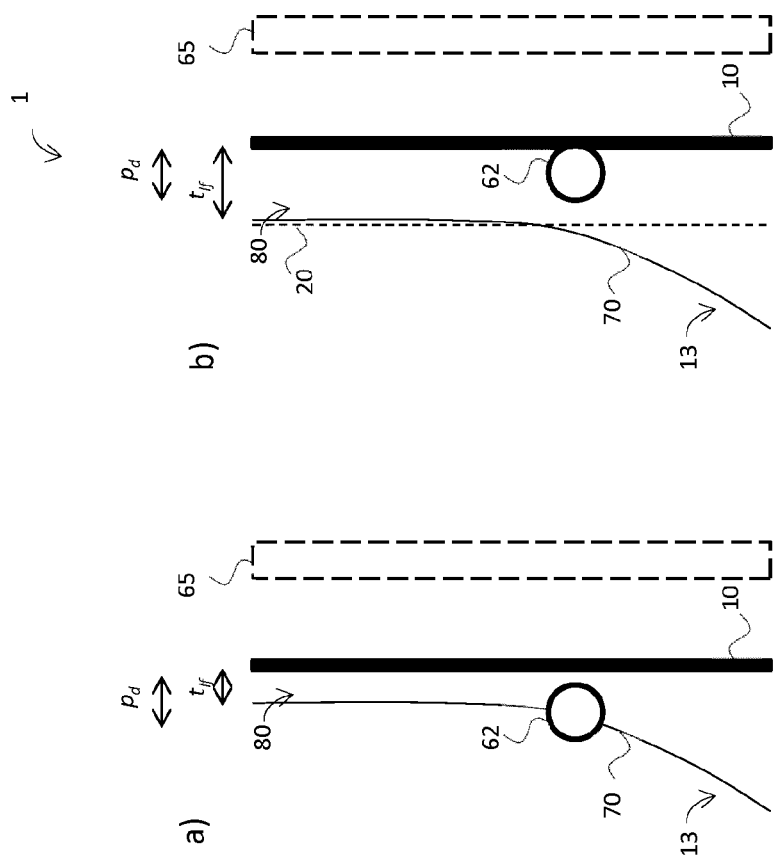
FIG. 5A shows a cross-sectional view of a draining meniscus shearing a particle away from a surface.
FIG. 5B shows a cross-sectional view of a particle shielded from a draining meniscus by a liquid film extending between a first rib and a second rib of a surface.

In addition to being influenced by the volume of space $v_{sp}$, thickness $t_{lf}$ of the capillarily retained portion 60 of bulk liquid 13 (and liquid film 80) may be influenced by the contact angle between the liquid-gas-solid interface, viscosity of the liquid, surface adsorption of the liquid, and the speed of the draining meniscus 70. Particles 62, or portion thereof, in the bulk liquid 13 received into the space 50 between first rib 20 and second rib 30 may be sheared from surface 10 when thickness $t_l$ is thinner than a diameter $p_d$ of particle 62. If the thickness $t_{lf}$ is less than diameter $p_d$ of particle 62 (or aggregate of particles), particle 62 may experience forces acting outwards from surface 10 thereby shearing particle 62 from surface 10 back into bulk liquid 13 (FIG. 5a). For example, under conditions typical in a cell separation process, an individual cell at a surface of a container, such as the wall of a tube, may be sheared from the surface through one or more forces of a meniscus during pour-off or aspiration of bulk liquid from the container.

Shearing of particle 62 from surface 10 and/or out of space 50 between first rib 20 and second rib 30 may be avoided if thickness $t_{lf}$ is greater than diameter $p_d$ of particle 62 (FIG. 5b). The foregoing may be effected by ensuring a sufficient velocity of a draining meniscus or by providing a surface 10 adapted with a plurality of ribs 15 for slowing drainage by creating a liquid film capillarily-retained between a first rib 20 and a second rib 30 on the surface 10. These and other strategies for increasing the thickness of the liquid film may be exploited either individually or synergistically.

However, optimization of particle separation or isolation performance involves more than simply maximizing the trailing film thickness as the bulk liquid is drained. On the one hand, a trailing film that is too thick may retain undesired particles that may be proximal to, but not necessarily in contact with, the surface—this may correspond to particles that were initially randomly distributed in the bulk solution as opposed to those urged into direct contact through, for example, magnetic forces. On the other hand, the thinner the trailing film the lower the recovery of the desired particles because they may be sheared off from the interface during bulk liquid drainage. Thus, the characteristics of the plurality of ribs on the surface may require optimization as described above in order to achieve a proper balance of capillary retention of a portion of the bulk liquid (ie. liquid film) to maximize subsequent particle recovery, and bulk liquid drainage to maximize the purity of subsequent particle recovery.

Indeed, because different particles may be present at different frequencies in a sample, such as a bulk liquid, the characteristics of the surface, ribs, or spaces therebetween may be further optimized for any given particle. For example, the optimum liquid film thickness may be modified based on the number and degree of particles to be retained at the surface within the spaces between the plurality of ribs. Further, the space between a first rib and a second rib may exclude larger particles from the liquid film and thus the excluded particle may be readily removed as the bulk liquid is removed away from the surface—even in the presence of a force urging the larger particle toward the surface. In this way size selection as well as specific magnetic tagging can be used to effect separation of particle mixtures.

Furthermore, at least a first portion of the particles 62 in the bulk liquid 13 may be received into the space 50 between the first rib 20 and the second rib 30, such as by applying a first force 65. Such first force 65 may urge the first portion of particles into the space between the first and second ribs, and at least a second portion of the particles urged into the space 50 are responsive to the first force 65. The first portion of particles and/or the second portion of particles may be entrained in liquid film 80 and therefore retained in the space 50 and in liquid film 80 by shielding them from one or more forces of a draining meniscus 70 as the bulk liquid 13 is removed away from the surface 10.

Once the bulk liquid 13 has been removed away from the surface 10, it may be desirable to resuspend in a buffer such portion of particles shielded by and entrained in liquid film 80. Thus, in one embodiment the plurality of ribs 15 on the surface 10 may shield the portion of particles 62 from the one or more forces exerted by the draining meniscus 70 as the bulk liquid 13 is removed away from the surface 10, but the plurality of ribs 15 may not impede the portion of particles from evacuating the space 50 in downstream steps of particle separation methods, such as in the absence of the first force 65.

Still further, the distribution of particles on a surface may affect the local liquid film thickness. Thus in another embodiment ribs may be dimensioned so that the liquid film thickness may be influenced by the ribs and not the distribution of particles at or near the surface. Decreasing the variance of target particle recovery by controlling the liquid film thickness and uniformity using surface ribs may be another advantage realized using this design concept.

Application in Particle and/or Cell Separation Methods

Figure 6:
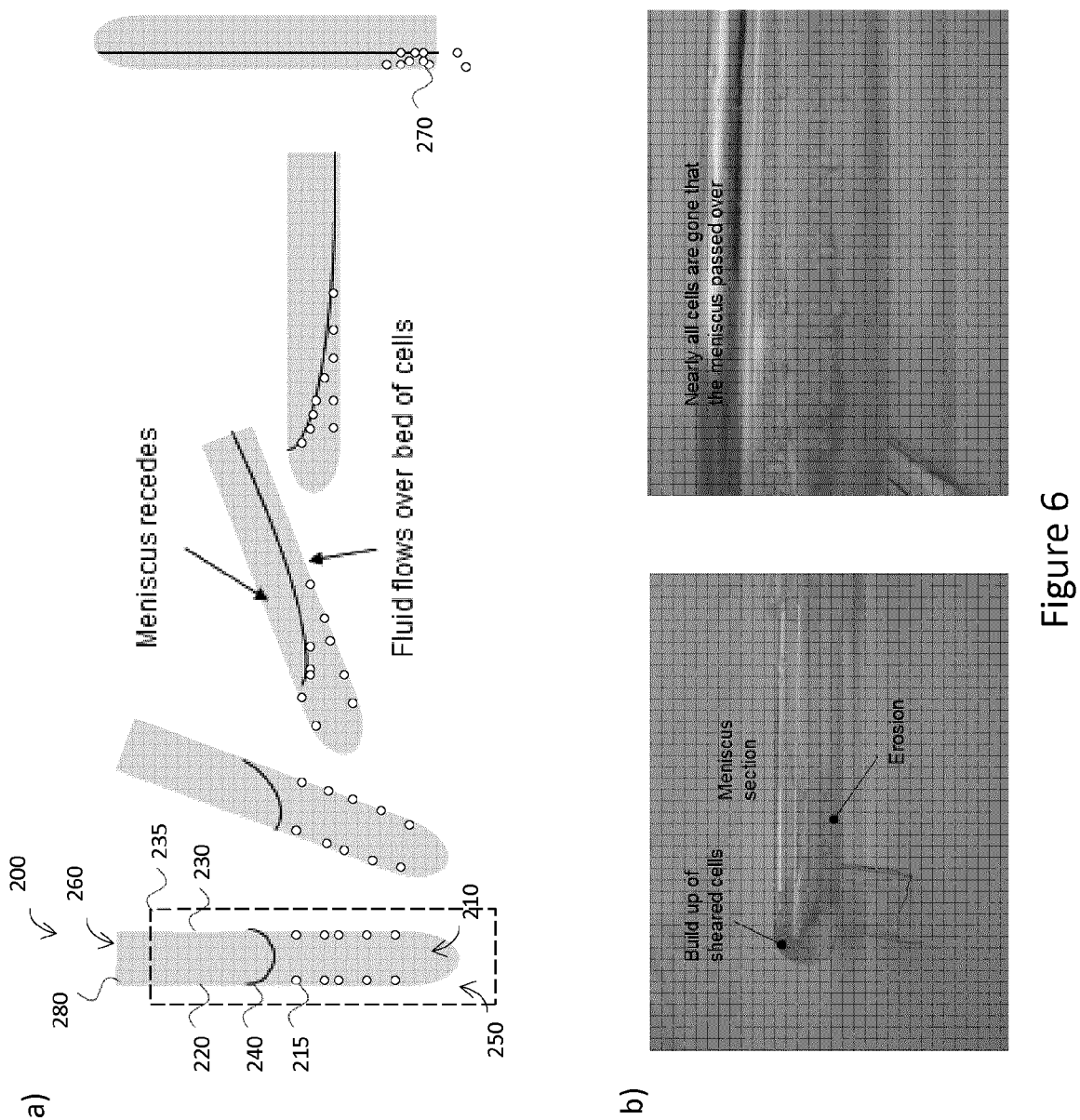
FIG. 6A shows a schematic representation of meniscus shear in pour-off methods of cell separation.

In preliminary particle and/or cell separation methods the meniscus shear effect was observed when using EASY-Sep™ (STEMCELL Technologies Inc.) in pour-off protocols (FIG. 6). Various aspects of an exemplary pour-off protocol of a liquid from a tube will be described below. In particular, the trajectory of the air-liquid interface (meniscus) is shown in FIG. 6a.

As can be seen in FIG. 6a, a tube 200 comprising a particle-containing bulk liquid 210 may be subjected to a method for separating particles from bulk liquid using the EASYSep™ (STEMCELL Technologies Inc.) system, or another system for separating particles from a bulk liquid. Particles and/or cells 215 may come into contact with an inner surface of tube 200, which may include a first sidewall 220 and a second sidewall 230, under the influence of a magnet 235 (subsequent steps of the depicted particle and/or cell separation method include but do not show magnet 235). As tube 200 is moved away from a vertical axis, bulk liquid 210 drains down first sidewall 220 of tube 200 and forms a meniscus 240 which may shear away particles and/or cells 215 from the inner surface thereof. Sheared particles 215 may be swept by draining meniscus 240 down to a bottom end 250 of tube 200. Once meniscus 240 has traversed first sidewall 220 and reached bottom end 250 of tube 200, a second phase of liquid removal begins wherein liquid 210 drains without a draining meniscus. In this phase of tube drainage, only weak liquid drag effects from the draining liquid urge particles and/or cells away from the surface. In the final stage of tube drainage, a meniscus traverses second sidewall 230 from bottom end 250 to an open upper end 260 thereof shearing particles and/or cells 215 from second sidewall 230 with high efficiency. This shear effect occurs in the final stages of tube drainage and causes the desired particles and/or cells to form a "last drop" 270 retained at a tube opening 280. At this point, tube drainage may be stopped in EASYSep™ (STEMCELL Technologies Inc.) protocols to retain the last drop comprising target particles and/or cells.

A conceptual model developed for EasySep™ (STEMCELL Technologies Inc.) identified the step of removing the bulk liquid from the tube using a pour-off or liquid aspiration step as problematic during cell separation methods. Indeed as outlined above, a draining meniscus traversing a substantially smooth surface comprising a compacted layer of cells may shear cells away from the surface. Such sheared-away cells may comprise the "last drop" after the bulk liquid is removed from the tube. To achieve satisfactory recovery following the EasySep™ (STEMCELL Technologies Inc.) protocol (see EasySep™ manual), the "last drop" should be retained after the bulk liquid is poured from the tube. If the "last drop" is lost during drainage of the tube, recovery for positive selection or purity for negative selection may be significantly negatively impacted.

In pour-off methods of bulk liquid removal, the draining meniscus affects only some of the sidewall(s) of the tube (FIG. 6b). As shown in FIG. 6b, PMBCs were positively selected using anti-CD45 magnetically-tagged antibodies. The tube was placed in a STEMCELL Silver magnet for 10 minutes, capped, the magnet was moved away from the vertical axis, and the tube was removed from the magnet prior to imaging. As also shown in FIG. 6b, a substantial fraction of cells have been stripped from a sidewall of the tube experiencing the draining meniscus. Also note, with aspiration methods of removing the bulk liquid, such as with Robosep™ (STEMCELL Technologies Inc.), the entire inner surface of a tube may be affected by the draining meniscus which can lead to drastically lower recoveries.

The problem of meniscus mediated shear of particles and/or cells in contact with a surface during pour-off or aspiration may be avoided in a method for separating particles from a bulk liquid by providing, as described hereinabove, a surface adapted with a plurality of ribs for capillarily retaining a liquid film on the surface. For example, the surface may be altered from a smooth surface design (henceforth denoted "F-tube" in the text) to a surface adapted with a plurality of ribs and spaces therebetween (denoted "G-tube"), as described in this disclosure.

An exemplary method may comprise contacting the surface with a bulk liquid comprising one or more particles, whereby the bulk liquid contacts the surface, the first and second ribs, and the space between the first and second ribs. Once the bulk liquid has come into contact with the surface, the plurality of ribs, and the space therebetween, at least a first portion of the particles in the bulk liquid may be received into the space between the first and second ribs.

Receiving the first portion of particles into the space between the first and second ribs may be passive or active. In embodiments where the receiving step is active, receiving may be carried out by applying a first force to urge the first portion of particles into the space between the first and second ribs. The first force may be a gravitational force, a magnetic attraction force, a pressure force, or any other force that may urge the movement of particles in a particular direction. In some embodiments, the particles received into the space may evacuate the space in the absence of the first force. Use of a first force may desirably separate the first portion of particles from other particles in the bulk liquid.

In embodiments where the first force is a magnetic attraction force, the responsive particles may have a first magnetic charge attracted to a magnet, such that the surface comprising the plurality of ribs is between the magnet and the bulk liquid whereby the first force urges the first portion of the particles toward the space. In such an embodiment, the responsive particles, if magnetic or magnetized, would respond to the first force causing such particles to be received into the space between the first and second ribs. As a specific example, a target cell may be connected by way of an immunoaffinity interaction (such as an antibody or a complex of antibodies ie. a tetrameric antibody complex) to one or more magnetizable particles, and under the influence of a magnetic force the target cell:particle complex(es) may be attracted toward the surface in the direction of the magnetic force.

Once the first portion of particles is received within the space between the first and second ribs, the bulk liquid may be removed away from the surface. When removing the bulk liquid away from the surface, a portion of the bulk liquid may be capillarily-retained between the first and second ribs to form a liquid film therebetween. The thickness of the liquid film between the first rib and the second rib, or the plurality of ribs, may be controlled or influenced as described more fully above.

Through the cooperating activity of the first and second ribs, or the plurality of ribs, and the liquid film, the particles received in the space therebetween may be entrained in the liquid film and thereby shielded from one or more forces of a draining meniscus as the bulk liquid is removed away from the surface. By shielding the particles entrained in the liquid film from the one or more forces of the draining meniscus, the particles are retained in the liquid film once the bulk liquid is removed away from the surface. Once the bulk liquid along with any contaminating or non-retained particles in the bulk liquid have been removed away surface, it may be desirable to isolate or resuspend the particles entrained in the liquid film. Resuspending the shielded particles entrained within the liquid film may be accomplished by adding an appropriate resuspension buffer against the surface or passively into a resuspension buffer by diffusion. Resuspension may further comprise removing the surface from the influence of the first force or applying a second force to urge the particles away from the surface and out of the space between the first and second ribs.

The skilled person will appreciate that as with many methods for separating particles from a bulk liquid the process may incorporate washing or rinse steps to enhance the purity of the separated particles.

A container having some or all of the desired features described above may take advantage of the capillary effect by placing ribs (e.g. parallel vertical ribs) around the inner perimeter of the container. Each rib connects with an inner perimeter of the tube surface to create a sharp edge enhancing capillary rise. In addition, the ribs help deflect the draining meniscus and thicken the liquid film to reduce the probability of the draining meniscus stripping cells from the wall. Similarly, liquid velocity in the spaces between the ribs may be lower, resulting in less drag force on cells at the surface. In addition, cells may remain hydrated while on the wall due to the capillary rise, reducing cell pinning and possible cell death due to dehydration and concomitant rise in ionic strength.

In another embodiment, improved performance may also be achieved using horizontal ribs, or helical ribs, similar to a screw thread, on the surface of the container. Cells should be retained during the liquid removal stage of cell separation, but it may be desirable to recover the cells afterwards by washing liquid down the container wall(s). Thus, in one preferred embodiment vertical ribs along the tube length may provide sufficient protection from a draining meniscus during liquid removal, but still allow for cells to be washed off the wall with rinsing.

The meniscus shear effects may be amplified in the ROBOSep™ (STEMCELL Technologies Inc.) protocols because the entire drainage process may be performed using aspiration through a pipette positioned at a bottom of the container. During such an aspiration mode, particles and/or cells brought into contact with a surface of a tube may be pulled away from the surface by the draining meniscus. As particles and/or cells are removed from the surface they may be entrained in the aspirating liquid and undesirably drawn out of the container. Such a stripping effect significantly reduces the recovery of particles and/or cells following the separation thereof from other particles and/or cells in the bulk liquid. Thus, a means in accordance with this disclosure of retaining cells on the container boundary may improve recovery of cells in positive cell selection protocols, or for maximal purity in negative cell selection protocols.

Thus, the disclosed apparatuses and the use thereof may improve particle and/or cell separation methods by controlling liquid film thickness as a draining meniscus traverses a surface. Such improvement to particle and/or cell separation methods may be evidenced by enhanced recovery and/or purity of particles and/or cells, as described herein.

Further, improvements to particle and/or cell separation methods using the apparatuses of the disclosure may be evidenced by prolonged viability of cells during cell separation procedures. After the particles and/or cells are brought into contact with the rib-modified surface (or inner surface of the container) and the bulk fluid has been removed away, whether by pour-off or by aspiration, the particles and/or cells are entrained in the liquid film. Such particles and/or cells maintain their viability longer than particles and/or cells having undergone a cell separation experiment using typical smooth-walled tubes. FIG. 7 shows that cell viability remains consistent over the duration of the experiment using the rib-modified tubes. In contrast, cell viability experiences a steady decline over the duration of the experiment using smooth-walled tubes. Such improved viability of cells entrained in the liquid film of rib-modified tubes may allow for longer protocols or "dry times" to be used as needed.

Still further, improvements to particle and/or cell separation methods using the apparatuses of the disclosure may be evidenced by a reduction in the number of steps (and therefore time and cost) of a cell separation procedure. In typical cell separation procedures, the particles and/or cells are brought into contact with a smooth surface (such as the inner surface of a container, such as a smooth-walled tube) under the influence of a force (such as a magnetic force) and the bulk fluid is removed away from the surface, while maintaining the influence of the force to hold the separated particles and/or cells in place. A buffer is then added to the tube and the contents of the tube are mixed causing many of the cells and/or particles to come off of the surface. The particle and/or cell-containing buffer is then incubated (under the influence of the force) to allow the cells and/or particles to re-migrate toward the surface. This process may be repeated any number of times in order to increase purities of the separated cells and/or particles, which may also have the effect of reducing overall recoveries of separated cells and/or particles. FIG. 8 shows that use of a rib-modified surface (or inner surface of a container) overcomes the need for performing such a sequence of separations. Rather, performing one or more gentle washes yields recoveries and purities of cells and/or particles that are comparable to a multi-separation approach. In contrast, one or more gentle wash steps (in place of a multi-separation approach) using a smooth surface (such as the smooth inner surface of a container) results in an undesirable reduction in the recovery of separated cells and/or particles, in comparison to a multi-separation approach.

An exemplary cross-sectional view of the rib-adapted G-tube is shown in FIG. 9a. The overall shape of the rib-adapted tube 300 (diameter, length, wall thickness, lip features) may be typical of standard smooth-walled plastic tubes used in existing cell separation practice (i.e. F-tubes). On an inner surface 310 of the G-tube 300, ribs 320 as described in this disclosure run axially along the length thereof. In one embodiment, ribs 320 start approximately 10 mm from an open end 325 of tube 300 and extend down toward a bottom end 340. Various embodiments were assessed by varying the cross-sectional shape of the ribs (e.g. square, triangular, rounded), height of the ribs (e.g. 250, 500, 1000 μm) and density of the ribs around the perimeter (e.g. 10, 30, or 60 ribs distributed around the perimeter). Rib density, and by extension the availability of spaces therebetween, may be adjusted depending on the expected proportion of target cells and/or particles contained in the bulk fluid. By tailoring the rib density based on the expected proportion of target cells and/or particles, it may be possible to enhance purities and recoveries of such target cells and/or particles during separation procedures. For example, having only sufficient space between ribs to accommodate cells and/or particles of interest (responsive to a force, such as a magnetic force), the cells and/or particles of interest may outcompete non-target cells and/or particles fortuitously in the spaces for portions of the surface most proximal to the influence of the force.

In pour-off protocols, both the standard smooth-walled F-tube and the modified G-Tube designs retain a significant amount of liquid which represents the "last drop" in EasySep™ (STEMCELL Technologies Inc.) protocols. The volumes are approximately 400 µL for the G-Tubes and 200 µL for the standard F-tube—suggesting that a G-Tube helps retain a thicker liquid film. FIG. 10a shows the retained volumes for 3 G-tube designs compared with the F-tube in pour-off mode. Two different drainage times (i.e. 2 seconds and 10 seconds) are also compared. As can be seen, both the rib density and the drainage time affect the final retained volume in the liquid film. FIG. 10b shows similar results for aspiration-mode drainage of the tube typical in RoboSep™ (STEMCELL Technologies Inc.) protocols. Under these conditions rib geometry, rib density and aspiration rate significantly contribute to liquid film thickness and retained liquid volume. At a high rib density, the retained liquid film may be on the order of the thickness observed during pour-off aspiration of the tube (i.e. 300 uL). With the F-tube, the retained film volume may be less than 10% of the retained volume with the G-tube. Further, the retained volume may be a strong function of rib density on the surface. At ½ the rib density, the retained volume may ⅔ that obtained with 500 um spacing, and at ¼ density less than ⅓ of the liquid volume may be retained. Thus, rib density can be used to modulate the apparent liquid film thickness.

When the aspiration rate is decreased, from 2 seconds for complete tube drainage to 10 seconds for complete drainage, the liquid film volume may also be significantly reduced. Thus, the rate the bulk liquid is aspirated from the G-tubes may also significantly affect liquid film volume. Note that for the F-tube, there was no significant effect of aspiration rate on final retained volume over this range. In both cases, the F-tube design only retained about 10% of the volume of the maximal retention volume of the G-tube design. Thus, the G-tube may afford an additional level of retained liquid film volume regulation through control of the aspiration rate.

During aspiration experiments it was noted that the aspiration pipette would occasionally become stuck to the bottom of rib-adapted tube 300 due to the aspiration vacuum. To circumvent this problem, a further innovation to tube 300 comprising a plurality of ribs 320 was developed in which a pair of ribs 330 may be added to the bottom 340 of tube 300. The pair of ribs 330 act as a pipette tip seat such that a vacuum could not form between tube bottom 340 and the aspiration pipette (FIG. 9b). In accordance with this innovation, the aspiration pipette may be rested directly on tube bottom 340 for maintaining consistent placement of the pipette) without causing pipette tip to become affixed to tube bottom during aspiration.

In further experiments the possibility of adding a diamagnetic additive to the bulk liquid to push non-magnetically-tagged cells away from the surface or container wall adjacent to a magnet was tested (i.e. out of the space between a first rib and a second rib). Diamagnetic liquids (e.g. Gadolinium) add an additional force to the cell separation process because the liquid may be more magnetic than the cell (and the volume that the cell occupies) a net repulsive force arises to move nonmagnetically-tagged cells away from a surface of a container adjacent to a magnet. Thus, the G-tubes and diamagnetic additive may operate synergistically. G-Tubes help retain liquid near the walls where the target cells accumulate during cell separation; the thicker the liquid film the higher the recovery of target cells as cells may be better protected from meniscus shear. However, with a thickened liquid film there may also be a higher retention of untagged cells randomly distributed within bulk liquid of the tube, and hence within the liquid film at the container wall. With the addition of a diamagnetic liquid, untagged cells may be urged away for the container wall adjacent to a magnet out of the capture volume of the liquid film. Thus, recovery of target cells can be increased by thickening the liquid film through modification of the wall geometry, while purity may be increased through a diamagnetic additive by pushing non-target cells away from the walls (FIG. 11a, 11b).

The apparatus and particle and/or cell separation methods of this disclosure provide rib-adapted surfaces that may help reduce meniscus stripping of particles and/or cells on a draining/filling surface by helping to protect particles and/or cells in contact with the surface in a liquid film formed by ribs adapted on the surface. The overall performance for both manual pour-off and automated pipetting may be improved in terms of (1) overall particle recovery and purity values, (2) increased start cell number range so that separation may be more effective at low cell numbers, (3) reduced variance in separation performance, (4) and faster separation times.

The following non-limiting examples provide further details which may help the skilled person understand the subject-matter disclosed herein.

ILLUSTRATIVE EXAMPLES

Example 1: Preliminary Prototype Manufacture

Figure 9:
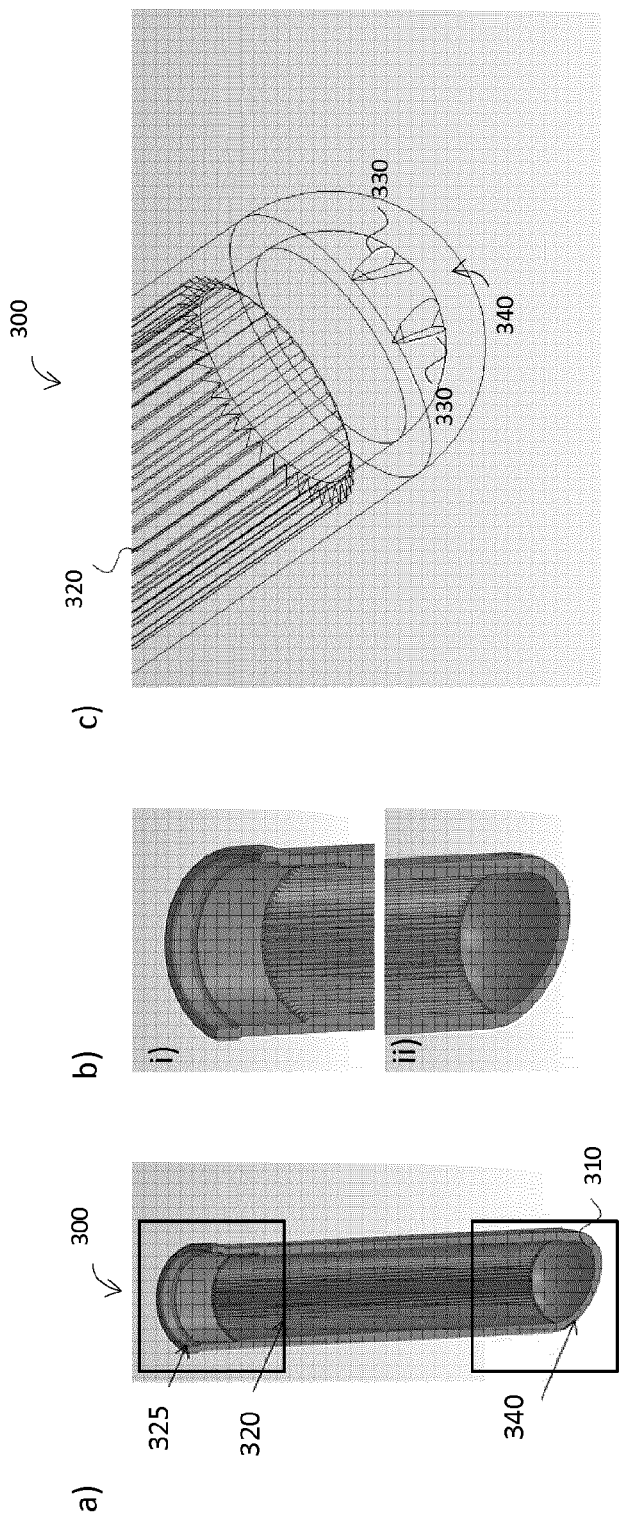

While any surface could be used to test the rib-adapted surface concept, initial testing focused on the 14 mL tube format which fits the EasySep™ Silver Magnet and may be used in RoboSep™ protocols. Other concepts were tested including Eppendorf-type (2 mL) and 50 mL tube sizes. FIG. 9 presents views of a prototype G-Tube. The overall shape (diameter, length, wall thickness, lip features) was replicated from the standard 14 mL F-tubes. Within the interior of the G-tube, the plurality of ribs run axially along the length thereof. Such ribs start approximately 13.5 mm from an open upper end of the tube and extend toward a hemispherical closed bottom end of the tube. Numerous designs were created by varying the shape of the ribs (square, triangular), height of the ribs (250, 500, 1000 µm) and spacing of the ribs (density). A possible embodiment may comprise 500 µm high square ribs with 900 µm pitch. Alternative embodiments may comprise triangular ribs or ribs having an apex width less than a cell diameter to address retention of cells on a top surface of the ribs.

Example 2: Volume Retention

Experiments were performed to measure and compare the volume retained in the smooth walled F-tubes and ribbed G-tubes following aspiration. Experiments were performed with protein containing (i.e. 10% newborn calf serum) phosphate buffered saline. First, 5 mL of liquid was added to each tube and then liquid was removed by either pour-off or aspiration; holding the inverted tube or the aspiration vacuum for a specified time of 2 or 10 s. The liquid remaining in the tube was measured using a mass balance. FIGS. 10a and 10b summarize the results.

In pour-off, both the F-tube and G-Tube designs retain a significant amount of liquid which represents the "last drop" typically retained in the EasySep™ protocol. The volumes are approximately 400 μL for the G-Tubes and 200 μL for the F-Tubes. Less liquid is retained when the tube is inverted for 10 s rather than 2 s as a few more drops fall from the tube in the intervening time. One interesting aspect of these results is the low variability in the volume retained during pour-off. Pour-off volume may be influenced by the balance between interfacial tension and the weight of liquid near the lip of the tube. For a drop to fall, its weight may exceed the interfacial tension forces. This relationship thus limits the amount of liquid that can be drained from the tube by pour-off.

For aspiration, the volume of a liquid retained decreases proportionally with rib density and converges with the F-tube (0 ribs) as expected. Unlike pour-off, where the retained volume is controlled by the balance between interfacial tension and weight, in aspiration the retained volume is controlled by capillarity of the ribs and drag as the liquid drains from the ribs. Therefore, retention volume is directly proportional to the number and dimensions of ribs on the surface. A larger volume retained in the tubes (ie. liquid film) may lower the purity of target cells as contaminating cells may reside in the retained volume. The presence of ribs may increase the retained liquid volume thereby reducing per-wash-purity if recovery of target cells remains constant. Careful design of the ribs is therefore required.

Example 3: Evaluation of Injection Moulded G-Tubes in RoboSep Aspiration Protocols (A) Experiments on a RoboSep™ unit were performed for CD19 positive cell selection using standard RoboSep™ operating procedures. The only difference in the experimental conditions was the tube used during separation. Three 0.5 mL donor samples were separated using the F-tubes and three 0.5 mL samples using the G-tubes. Table 1 presents target cell recoveries for each tube type. In this demonstration, purities were relatively unaffected while target cell recovery increased more than 2-fold.

TABLE 1

| Tube Type | % Purity | % Recovery |
| --- | --- | --- |
| F-Tube - 1 | 95.1 | 37.27 |
| F-Tube - 2 | 91.2 | 28.65 |
| F-Tube - 3 | 87.6 | 41.14 |
| G-Tube - 1 | 95.5 | 84.85 |
| G-Tube - 2 | 94.7 | 76.78 |
| G-Tube - 3 | 88.3 | 87.41 |

(B) Experiments on a RoboSep™ unit were performed for CD56 positive cell selection using standard RoboSep™ operating procedures. The only difference in the experimental conditions was the tube. Three 0.5 mL donor samples were separated using the F-tubes and three 0.5 mL samples using the G-tubes. Table 2 presents target cell recoveries for each tube type. In this demonstration purities were relatively unaffected while target cell recovery increased more than 3-fold. Further, the general applicability of this design to different cell-types selection is confirmed.

TABLE 2

| Tube Type | % Purity | % Recovery |
| --- | --- | --- |
| F-Tube - 1 | 97.5 | 16.7 |
| F-Tube - 2 | 95.5 | 19.02 |
| F-Tube - 3 | 97.2 | 19.94 |
| G-Tube - 1 | 97.4 | 56.94 |
| G-Tube - 2 | 96.5 | 61.03 |
| G-Tube - 3 | 98 | 62.15 |

(C) Experiments on a RoboSep unit were performed for CD3 positive selection using standard RoboSep operating procedures. The only difference in the experimental conditions was the tube design. Three 0.5 mL donor samples were separated using the F-tubes and three 0.5 mL samples using the G-tubes. Table 3 presents average target cell recoveries for each tube type. In this demonstration purities were relatively unaffected while target cell recovery increased more than 1.5-fold. However, this example also demonstrates the slight loss in purity achieved with the increased volume retention of the G-tube design.

TABLE 3

| Tube Type | % Purity | % Recovery |
| --- | --- | --- |
| F-Tube - 1 | 99.6 | 40.5 |
| G-Tube - 1 | 95.5 | 66.0 |

Example 4: Comparison of Tube Surface Design Using Releasable Particles in RoboSep Procedures Experiments on a RoboSep™ unit were performed for CD19 positive selection using standard RoboSep™ operating procedures. The only difference in the experimental conditions was the tube design. Four 0.5 mL donor samples were separated in triplicate using F-tubes and three different rib density G-tube designs. In this experiment the rib density on the wall was compared to optimize the performance of the G-Tube. In each case three replicate samples were separated and purity and recovery estimated (Table 5). Here the rib density on the surface was not found to significantly affect the purity of the final CD19 positive selection. However, rib density significantly impacts the recovered fraction of CD19 positive cells. It was found that as the rib density increases the recovered fraction also increases. The maximum rib density tested (60 ribs per tube) provided significantly higher recovery fraction than the 15 or 30 rib tube designs ($P<0.0001$).

TABLE 4

| | % Purity | % Recovery | Cells |
| --- | --- | --- | --- |
| R1Q1 - Std | 99.2 | 7.4 | 6.50E+05 |
| R2Q2 - Std | 98.4 | 9.2 | 8.13E+05 |
| R3Q3 - Std | 99.3 | 11.6 | 1.02E+06 |
| R1Q2 - 15 | 99.5 | 24.2 | 2.13E+06 |
| R2Q3 - 15 | 99.1 | 24.7 | 2.18E+06 |
| R3Q4 - 15 | 99 | 26.0 | 2.29E+06 |
| R1Q3 - 30 | 99.6 | 21.1 | 1.86E+06 |
| R2Q4 - 30 | 99.3 | 28.1 | 2.48E+06 |
| R3Q1 - 30 | 99.3 | 24.6 | 2.17E+06 |
| R1Q4 - 60 | 99.4 | 30.0 | 2.64E+06 |
| R2Q1 - 60 | 99.1 | 28.3 | 2.49E+06 |
| R3Q2 - 60 | 99.3 | 31.5 | 2.77E+06 |

TABLE 4-continued

|   |   | % Purity | % Recovery | Cells |
|---|---|---|---|---|
| Average | STD | 99.0 | 9.4 | 8.3E+05 |
|   | 15 | 99.2 | 25.0 | 2.2E+06 |
|   | 30 | 99.4 | 24.6 | 2.2E+06 |
|   | 60 | 99.3 | 30.0 | 2.6E+06 |

Example 5: G-Tube Synergy with Diamagnetic Additives

Experiments were performed to evaluate synergistic effects of using G-Tubes with a diamagnetic additive (Gadolinium) in magnetically-tagged cell purification. G-Tubes help retain a liquid film on the tube wall where target cells accumulate adjacent to a magnet during cell separation. At the same time a diamagnetic additive such as chelated-$Gd^{2+}$ pushes non-target, untagged cells away from the tube wall adjacent to the magnet. The counter flow of tagged and non-tagged cells in this separation may improve the purity of target cells in the liquid film following bulk liquid aspiration. FIGS. 11a and 11b plot the data from two separate experiments with CD3+ and CD19+ selection respectively. Similar results were found in further replicate experiments. These experiments involved direct comparisons between F-Tubes and G-Tubes, and pour-off vs aspiration liquid fractionation methods. Clearly the diamagnetic additive can compensate for the loss of cell purity due to the increase in retained volume with G-tubes, while maintaining the increase in recovery due to the slowed surface drainage as a result of the surface ribs. Some observations are summarized below:

For the diamagnetic additive the improvement in purity was significant ($p<0.0001$, $p<0.0001$), but did not significantly change the recovery ($p=0.12$, $p=0.68$).

The diamagnetic additive worked with pour-off which was unexpected as the mixing created during tube inversions may be considered to have a disruptive effect on the separation. Thus, diamagnetic additives might be used to improve purity.

The relative improvement for the G-tubes with and without the additive is greater (~1.0 logit Purity) compared to the F-tubes (~0.5 logit Purity)

Therefore, the diamagnetic additive improves purity for both the F-Tubes and G-Tubes, in both pour-off and aspiration methods, without negatively impacting recovery. However, the relative improvement in purity is larger in the G-Tubes confirming that a synergistic effect is present.

What is claimed is:

1. An apparatus for separating particles from a bulk liquid, the apparatus comprising:
a container having:
a surface to be contacted by a particle-containing bulk liquid,
a plurality of ribs on the surface, each rib of the plurality of ribs being positioned between and spaced apart from two adjacent ribs on the surface by a substantially uniform pitch distance; and
a space between each rib and each of the two adjacent ribs being dimensioned to capillarily retain therebetween a portion of the bulk liquid and at least a portion of the particles entrained therein when the liquid contacting the surface is removed away from the surface,
wherein the surface is an inner sidewall of the container extending from an upper end having an opening to a bottom wall opposed to the opening, and the plurality of ribs extend away from the inner sidewall toward an interior of the container, and
wherein the container is a tube, and
wherein the plurality of ribs extend in a direction between the opening and the opposed bottom wall along the inner sidewall and are distributed around an inner perimeter of the sidewall of the tube and the pitch distance is less than about 1 mm.

2. The apparatus according to claim 1, wherein a first rib extends along a first longitudinal axis, and wherein a second rib extends along a second longitudinal axis.

3. The apparatus according to claim 2, wherein the second longitudinal axis is substantially parallel to the first longitudinal axis.

4. The apparatus according to claim 3, wherein the first longitudinal axis and the second longitudinal axis are generally linear.

5. The apparatus according to claim 1, wherein a first rib includes a first sidewall extending away from the surface and having a first base edge and a first protruding edge, and a second sidewall extending away from the surface and having a second base edge and a second protruding edge, the first base edge spaced apart from the second base edge by a first rib width and the first protruding edge connected to the second protruding edge at a first apex height, and wherein a second rib includes a third sidewall extending away from the surface and having a third base edge and a third protruding edge, and a fourth sidewall extending away from the surface and having a fourth base edge and a fourth protruding edge, the third base edge spaced apart from the fourth base edge by a second rib width and the third protruding edge connected to the fourth protruding edge at a second apex height.

6. The apparatus according to claim 5, wherein the first apex height and the second apex height are each between about 20 um to about 1 mm.

7. The apparatus according to claim 5, further comprising a third rib spaced apart from the second rib by the pitch distance, the third rib including a fifth sidewall extending away from the surface and having a fifth base edge and a fifth protruding edge, and a sixth sidewall extending away from the surface and having a sixth base edge and a sixth protruding edge, the fifth base edge spaced apart from the sixth base edge by a third rib width and the fifth protruding edge connected to the sixth protruding edge at a third apex height.

8. The apparatus according to claim 7, wherein the third apex height is between about 20 um and about 1 mm and is different than the first and second apex heights.

9. The apparatus according to claim 7, wherein the first protruding edge is connected to the second protruding edge by a first top wall, and the third protruding edge is connected to the fourth protruding edge by a second top wall.

10. The apparatus according to claim 9, wherein the fifth protruding edge is connected to the sixth protruding edge by a third top wall.

11. The apparatus according to claim 10, wherein a width of the first top wall, the second top wall and the third top wall is between about 1 um and about 1 mm.

12. The apparatus according to claim 1, wherein the pitch distance is at least 1 um.

13. The apparatus according to claim 5, wherein the first rib has a first cross-sectional shape taken in a plane orthogonal to the first longitudinal axis and the second rib has a second cross-sectional shape taken in the plane.

14. The apparatus according to claim 13, wherein the first cross-sectional shape is the same as the second cross-sectional shape.

15. The apparatus according to claim 13, wherein the first cross-sectional shape is a quadrilateral.

16. The apparatus according to claim 13, wherein the first cross-sectional shape is a triangle.

17. The apparatus according to claim 9, wherein the first top wall and the second top wall are coplanar with the inner surface of the container.

18. The apparatus according to claim 2, wherein the first and second ribs extend a rib length along a surface longitudinal axis, and wherein the rib length is between 5% and 95% of the surface longitudinal axis.

19. A container for holding a particle-containing bulk liquid, the container comprising:
   a closed bottom end having a bottom wall, an open upper end, one or more sidewalls extending from the bottom wall to the upper end along a longitudinal axis in a direction from the open upper end to the closed bottom end, and an inner surface bounding an interior of the container and an opposed outer surface;
   a plurality of ribs on the inner surface, the plurality of ribs comprising a pair of end ribs extending parallel to opposed edges of the inner surface and a plurality of intervening ribs flanked by the pair of end ribs, wherein each rib of the plurality of intervening ribs (i) is spaced apart from two adjacent ribs by a substantially uniform pitch distance, (ii) extends in a direction along the longitudinal axis, and (iii) extends away from the inner surface toward an interior of the container; and
   a substantially uniform space between adjacent ribs of the plurality of ribs,
whereby when bulk liquid is contained in the interior of the container the bulk liquid contacts the inner surface, the plurality of ribs, and the spaces there, and whereby the plurality of ribs are dimensioned to capillarily-retain therebetween a portion of the bulk liquid and at least a portion of the particles entrained therein when the bulk liquid contacting the surface is removed away from the surface.

20. A method for separating particles from a particle-containing bulk liquid in a container having a surface that is an inner sidewall extending from an upper end having an opening to a bottom wall opposed to the opening, a plurality of ribs extending along the inner sidewall and away from the inner sidewall toward an interior of the container, each rib of the plurality of ribs being positioned between and spaced apart from two adjacent ribs on the surface by a uniform pitch distance sufficient to receive a diameter of at least one particle, and a space between the first rib and the second rib, the method comprising:
   contacting the inner sidewall with the particle-containing bulk liquid, whereby the particle-containing bulk liquid contacts the surface, the first and second ribs, and the space between the first and second ribs;
   receiving at least a portion of the particles in the particle-containing bulk liquid into the space between the first and second ribs;
   removing, by pour-off, pipetting or aspiration, the particle-containing bulk liquid away from the surface in a direction along the axis in which each of the plurality of ribs extend, a portion of the particle-containing bulk liquid received in the space being capillarily-retained in the space between the first and second ribs to form a liquid film on the inner sidewall;
   shielding the particles of the portion of the particle-containing bulk liquid retained in the space between the first and second ribs by being entrained in the liquid film from one or more forces of a draining meniscus as residual bulk liquid and any residual particles therein is removed away from the surface; and
   resuspending in a buffer the shielded particles entrained within the liquid film,
wherein the container is a tube comprising one sidewall and the plurality of ribs extend in a direction between the opening and the opposed bottom wall along the sidewall.

* * * * *